United States Patent
McGuigan et al.

(10) Patent No.: US 8,762,164 B2
(45) Date of Patent: *Jun. 24, 2014

(54) COMPUTER SYSTEM AND METHOD FOR GENERATING HEALTHCARE RISK INDICES USING MEDICATION COMPLIANCE INFORMATION

(75) Inventors: Kimberly A. McGuigan, Ridgewood, NJ (US); Debra A. Maldonato, Chestnut Ridge, NY (US); Qingshan Qian, Los Angeles, CA (US); Kurtis W. Andrews, Chestnut Ridge, NY (US); Keith J. Bradbury, Blauvelt, NY (US); George Fulop, Mount Kisco, NY (US); Joseph A. Boscarino, Ramsey, NJ (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/786,125

(22) Filed: May 24, 2010

(65) Prior Publication Data
US 2010/0228570 A1 Sep. 9, 2010

Related U.S. Application Data

(62) Division of application No. 10/689,852, filed on Oct. 22, 2003, now Pat. No. 7,725,327.

(51) Int. Cl.
*G06Q 10/00* (2012.01)
*G06Q 50/22* (2012.01)
*G06F 19/00* (2011.01)
*G06Q 50/24* (2012.01)

(52) U.S. Cl.
CPC ............ *G06Q 50/22* (2013.01); *G06F 19/3431* (2013.01); *G06Q 50/24* (2013.01)
USPC ...................................... 705/2; 705/3; 705/4

(58) Field of Classification Search
USPC ..................... 705/2–3, 37; 368/10; 382/190
See application file for complete search history.

(56) References Cited

U.S. PATENT DOCUMENTS

| | | | |
|---|---|---|---|
| 4,588,303 A * | 5/1986 | Wirtschafter et al. | 368/10 |
| 4,667,292 A | 5/1987 | Mohlenbrock et al. | |
| 5,018,067 A | 5/1991 | Mohlenbrock et al. | |
| 5,325,293 A | 6/1994 | Dorne | |
| 5,640,468 A * | 6/1997 | Hsu | 382/190 |

(Continued)

*Primary Examiner* — Valerie Lubin
(74) *Attorney, Agent, or Firm* — Husch Blackwell LLP

(57) ABSTRACT

A healthcare risk index is generated using a patient or individual's pharmacy claims. The index may be used to explain and predict variation in pharmacy-related costs and variation in total healthcare costs or utilization. In particular, the index is generated by first examining the individual's pharmacy claims to identify any chronic conditions possessed by the individual. Similarly, the individual's pharmacy claims are examined to identify any compliance medications prescribed to the individual. The chronic condition information is used to generate a chronic condition score by summing regression coefficients for each chronic condition possessed by the individual. Likewise, the compliance medication information is used to generate a compliance medication score by summing products of regression coefficients for each compliance medication prescribed to the individual with associated medication supply weights. From there, a modified chronic condition score is generated by multiplying the chronic condition score by an overall chronic condition regression coefficient. The modified chronic condition score may then be further modified by subtracting a no-claims weight from the chronic condition score in cases where the individual has no pharmacy claims. Finally, the risk index may be determined by summing the modified chronic condition score and the compliance medication score.

11 Claims, 9 Drawing Sheets

(56) References Cited

U.S. PATENT DOCUMENTS

| | | |
|---|---|---|
| 6,410,335 B1 | 6/2002 | Pollak et al. |
| 6,468,210 B1 | 10/2002 | Iliff |
| 6,578,003 B1 | 6/2003 | Camarda et al. |
| 7,136,055 B2 | 11/2006 | Kamijo |
| 7,444,291 B1 | 10/2008 | Prasad et al. |
| 7,640,175 B1 * | 12/2009 | Prasad et al. .................. 705/3 |
| 7,725,327 B2 | 5/2010 | McGuigan et al. |
| 2001/0020229 A1 * | 9/2001 | Lash ................ 705/3 |
| 2002/0194114 A1 * | 12/2002 | Erdmier ................ 705/37 |

\* cited by examiner

| CATEGORY | CHRONIC CONDITIONS | WEIGHTS |
|---|---|---|
| XA | ACID PEPTIC DISORDERS | 10.3039 |
| XB | TREATMENT FOR ACNE | 10.6623 |
| XC | ATTENTION DEFICIT/HYPERACTIVITY DISORDER (UNDER 18) | 13.9197 |
| XD | ADVANCED LIVER DISEASE | 0.54999 |
| XE | AIDS | 31.9221 |
| XF | ALLERGIC RHINITIS | 10.1509 |
| XG | AMYOTROPHIC LATERAL SCHLEROSIS (LOU GEHRIG'S DISEASE) | 29.0981 |
| XH | ALZHEIMER'S DISEASE | 6.54956 |
| XI | ANGINA / CORONARY ARTERY DISEASE) | 0.067019 |
| XJ | ANXIETY DISORDER / PANIC DISORDER / SOCIAL PHOBIA | 3.17593 |
| XK | ARRHYTHMIA | 6.09765 |
| XL | ASTHMA (UNDER 55) | 9.0274 |
| XM | BENIGN PROSTATIC HYPERPLASIA | 7.97429 |
| XN | CANCER (ANY TYPE) | 10.8211 |
| XO | CONGESTIVE HEART FAILURE | 2.18044 |
| XP | CHRONIC OBSTRUCTIVE PULMONARY DISEASE (55+) | 3.57019 |
| XQ | CYSTIC FIBROSIS | 5.16423 |
| XR | DEPRESSION | 10.3768 |
| XS | DIABETES TYPE I - INSULIN DEPENDENT | 9.019 |
| XT | DIABETES TYPE II - NON-INSULIN DEPENDENT | 7.29497 |
| XU | END STAGE RENAL DISEASE (ESRD) | 12.5402 |
| XV | EPILEPSY | 6.93106 |
| XW | GAUCHER'S DISEASE | 83.2477 |
| XX | GLAUCOMA | 2.31705 |
| XY | GOUT | 1.98149 |
| XZ | GROWTH HORMONE DEFICIENCY | 32.512 |
| XAA | HEPATITIS B | 4.09929 |
| XBB | HEPATITIS C | 33.2874 |
| XCC | HIGH CHOLESTEROL / TRIGLYCERIDES | 10.7383 |
| XDD | HYPERTENSION | 8.30913 |
| XEE | HYPOTHYROIDISM | 1.21422 |
| XFF | INFLAMMATORY BOWEL DISEASE | 8.56743 |
| XGG | MANIC DEPRESSIVE | 4.62228 |
| XHH | MIGRAINE | 8.26695 |
| XLL | MULTIPLE SCLEROSIS | 30.5853 |
| XMM | ORGAN TRANSPLANTATION | 17.0153 |
| XNN | MENOPAUSE (HORMONE REPLACEMENT THERAPY) (45-59) | 7.26419 |
| XOO1 | OSTEOPOROSIS (BONE RESORPTION SUPPRESSION AGENTS ) (60+) | 6.69366 |
| XOO2 | OSTEOPOROSIS (ESTROGENIC AGENTS) (60+) | 3.50463 |
| XPP | PARKINSON'S DISEASE | 8.11787 |
| XQQ | PERIPHERAL VASCULAR DISEASE | 1.76236 |
| XRR | PSORIASIS | 9.92265 |
| XSS | PSYCHOTIC DISORDERS / DEMENTIA AND NO ANTIDEPRESSANTS (65+) | 4.5396 |
| XTT | RHEUMATOID ARTHRITIS | 10.5781 |
| XUU | SCHIZOPHRENIA (UNDER 65) | 13.8768 |
| XVV | SMOKING CESSATION | 3.40704 |
| XWW | THROMBOEMBOLYTIC DISEASE I (PLATELET AGGREGATION INHIBITORS) | 1.44029 |
| XKK | THROMBOEMBOLYTIC DISEASE II (ORAL ANTICOAGULANTS, COUMARIN TYPE) | 2.83761 |
| XYY | TUBERCULOSIS | 5.049 |
| XZZ | URINARY INCONTINENCE | 3.66661 |

FIG. 6

| COMPLIANCE MEDICATION | WEIGHTS FOR LOG INDEX | WEIGHTS FOR SQUARE ROOT INDEX |
|---|---|---|
| CHRONIC CONDITION SCORE | 0.08036 | 0.65876 |
| NOCLAIM | -2.24249 | -5.42877 |
| ASTHMA MEDICATIONS | 0.00734 | 0.07566 |
| ASTHMA CONTROLLERS | 0.00246 | 0.0642 |
| CONGESTIVE HEART FAILURE MEDICATIONS | -0.00095396 | 0.00615 |
| ANGIOTENSION CONVERTING ENZYMES | 0.00183 | 0.00987 |
| GASTROINTESTINAL MEDICATIONS | -0.00041974 | 0.04681 |
| PROTON PUMP INHIBITORS | 0.0049 | 0.07727 |
| HIGH CHOLESTEROL MEDICATIONS | 0.00020414 | 0.01141 |
| STATINS | 0.00339 | 0.04491 |
| DIABETES MEDICATIONS | -0.0001036 | 0.07623 |
| DIABETES TYPE 2 MEDICATIONS | 0.00285 | 0.06342 |
| DEPRESSION MEDICATIONS | 0.00358 | 0.07158 |
| HYPERTENSION MEDICATIONS | 0.00811 | 0.04302 |

FIG. 7

COMPUTER SYSTEM AND METHOD FOR GENERATING HEALTHCARE RISK INDICES USING MEDICATION COMPLIANCE INFORMATION

CROSS REFERENCE TO RELATED APPLICATION

This application is a divisional patent application of U.S. patent application Ser. No. 10/689,852, filed on Oct. 22, 2003, and issued on May 25, 2010, as U.S. Pat. No. 7,725,327, which is hereby incorporated by reference herein in its entirety.

BACKGROUND OF THE INVENTION

1. Field of the Invention

The present invention is directed to computer-related and/or assisted systems, methods, and computer program devices for facilitating efficient and effective healthcare management programs. More particularly, the present invention relates to techniques for generating a risk index which may be used for clinical case identification, such as e.g., disease management programs, to explain and predict variation in pharmacy-related costs, and to explain and predict variation in total healthcare costs or utilization.

2. Description of the Related Art

A major economic problem that has surfaced during the past twenty years has been the upward spiraling cost of medical care. Demographic factors have played one role in this increased cost since extended life expectancies increase the percentage of older individuals in the population. Generally, such individuals require a much higher degree of medical care.

A second major factor contributing to increased costs for medical care has been the advent of many new, expensive, medical procedures which have sprung from medical and instrumentation advances of the past ten years. More widely known examples are organ transplants and the use of CAT scanners or MRI units for routine diagnosis.

An additional factor resulting in these increased costs has been the increased rate of inflation, which has dramatically influenced the costs for drugs. Due to all of the above, as well as other factors, the cost of even routine medical care has increased dramatically.

Correspondingly, increasing numbers of healthcare studies have been commissioned with the stated goal of optimizing healthcare services and expenditures. For instance, numerous methods and techniques have been proposed, which attempt to increase healthcare efficiency by predicting healthcare costs.

For example, U.S. Pat. No. 4,667,292, issued to Mohlenbrock, et al., in 1987, and incorporated herein by reference, discloses a medical reimbursement computer system which generates a list identifying the most appropriate diagnostic-related group (DRG) and related categories applicable to a given patient for inpatient claims (see, e.g., STEPS 33-65 of Prior Art FIG. 11). The list is limited by a combination of the characteristics of the patient and an initial principal diagnosis. A physician can choose a new designation from a list of related categories while the patient is still being treated. Manually determined ICD-9 numbers can then be applied to an available grouper computer program to compare the working DRG to the government's DRG. This information may be used in conjunction with predicting healthcare costs.

U.S. Pat. No. 5,018,067, also issued to Mohlenbrock, et al., in 1991, and incorporated herein by reference, discloses an apparatus and method for improved estimation of healthcare resource consumption through the use of diagnostic and/or procedure-grouping and severity of illness indicators. This system is a computer-implemented program that calculates the amount of payment to a health provider by extracting the same input data as that identified in the Mohlenbrock '292 Patent (which discloses the DRG System). The system calculates the severity of the patient's illness then classifies each patient into sub-categories of resource consumption within a designated DRG. A computer combines the input data according to a formula consisting of constants and variables. The variables are known for each patient and relate to the number of ICD codes and the government weighing of the codes. The software program determines a set of constants for use in the formula for a given DRG which minimizes variances between the actual known outcomes and those estimated by use of the formula. Because it is based upon various levels of illness severity within each diagnosis, the results of this system provide a much more homogenous grouping of patients than is provided by the DRGs. Providers can be compared to identify those providers whose practice patterns are of the highest quality and most cost efficient. A set of actual costs incurred can be compared with the estimated costs. After the initial diagnosis, the system determines the expected costs of treating a patient.

U.S. Pat. No. 5,325,293 to Dorne, issued in 1994, and incorporated herein by reference, discloses a system and method for correlating medical procedures and medical billing codes. After an examination, the system automatically determines raw codes directly associated with all of the medical procedures performed or planned to be performed with a particular patient. The system allows the physician to modify the procedures after performing the examination. By manipulating the raw codes, the system generates intermediate and billing codes without altering the raw codes.

While useful in their own ways, the techniques disclosed in the above-described prior art references, however, fail to meet all of the needs of today's healthcare community. For example, it has been determined by the inventors of the present invention that each of the techniques described above fail to consider the predictive nature of pharmacy claims-based data (e.g., the ability to predict and explain variation in costs using claims data). As a result, the prior art methods fail to address situations where patients refill prescriptions without visiting a physician's office (e.g., where patients refill prescriptions based on a number of refills given with an initial prescription).

Thus, none of the techniques described above, make use of pharmacy claims data to predict, e.g., healthcare costs. More particularly, it has been determined by the inventors of the present invention that these and other prior art techniques fail to consider the predictive qualities possessed by a patient's pharmacy claims. Furthermore, these and other prior art techniques fail to consider the predictive nature of a patient's compliance with specific pharmaceuticals.

What is therefore needed is a technique that predicts risk based on chronic conditions possessed by an individual patient as determined according to the individual's pharmacy claims information.

Furthermore, it has been determined by the inventors of the present invention that a need also exists for a technique that predicts risk based on an individual patient's compliance with instructions provided on those medications.

SUMMARY OF THE INVENTION

The present invention is directed to generating a healthcare risk index using a patient's or individual's pharmacy claims, which are indicative of, for example, chronic conditions possessed by the individual, the individual's compliance on certain medications, and situations where the individual has no pharmacy claims whatsoever. The index may be used to explain and predict variation in pharmacy-related costs and variation in total healthcare costs or utilization.

Various considerations and/or factors may be used in creating the healthcare risk index. One example of the method used to create the healthcare index includes first examining the individual's pharmacy claims to identify any chronic conditions possessed by that individual. Similarly, the individual's pharmacy claims are examined to identify any compliance medications prescribed to the individual. The chronic condition information is used to generate a chronic condition score by summing regression coefficients for each chronic condition possessed by the individual. Likewise, the compliance medication information is used to generate a compliance medication score by summing products of regression coefficients for each compliance medication prescribed to the individual with associated medication supply weights. From there, a modified chronic condition score is generated by multiplying the chronic condition score by an overall chronic condition regression coefficient. The modified chronic condition score may then be further modified by subtracting a no-claims weight from the chronic condition score in cases where the individual has no pharmacy claims. Finally, the risk index may be determined by summing the modified chronic condition score and the compliance medication score. Any variation of the above method may alternatively be used that considers similar, additional and/or other factors in determining the healthcare risk index.

One embodiment of the present invention is now summarized. In particular, a compliance-based risk index is generated using pharmacy claims to estimate risk. More specifically, the compliance-based risk index represents a pharmacy claims-based co-morbidity risk index. The index was developed to allow accurate comparisons between various populations by adjusting for a "burden of illness." In addition, the index may be used to predict future medical costs, total healthcare costs, and probability and amounts of future medical services utilization.

In use, individual patients (e.g., members of a particular healthcare insurance plan) receive risk scores based on chronic medications used, as well as their compliance on those medications. Scores increase, for example, with the number of diseases present, with more costly diseases receiving higher scores. In addition, plan members with non-chronic acute medication use are distinguished from those with no utilization. In one embodiment, the risk index was developed using patient information from a conventional pharmacy claims database and from patient eligibility data. In other embodiments, other pharmacy claims databases, along with patient eligibility information, may be utilized in conjunction with the present invention. For example, database information provided by any health insurer or pharmacy benefits manager may just as easily be utilized. In any event, scoring is based on values obtained from these data sources.

The uses of such a compliance-based risk index are many. For example, the index may be used for research and actuarial purposes, such as clinical case identification uses (e.g., disease management programs). Similarly, the index may be used to explain and predict variation in pharmacy-related costs and variation in total healthcare costs or utilization. Further, the index may be used as a tool in program evaluation to create comparable groups to adjust for factors such as adverse or favorable selection into healthplans, programs or health-related interventions.

Thus, the compliance-based risk index of the present invention advantageously solves, for example, three problems: clinical case identification/disease management, prediction of concurrent and prospective pharmacy-related and total healthcare costs, and allows the comparison of groups which may have differing rates of chronic illness.

The probability sample, which in one embodiment is a pharmacy claims database, was used to develop the index. More particularly, the pharmacy claims from the data source are first reviewed to determine which conditions exist for each patient and indicator variables are set if the conditions exist. Sample chronic conditions indicator weights are provided in Table I (shown below).

TABLE I

| Category | Chronic Conditions | Weights |
|---|---|---|
| XA | Acid Peptic Disorders | 10.3039 |
| XB | Treatment for acne | 10.6623 |
| XC | Attention Deficit/Hyperactivity Disorder (under 18) | 13.9197 |
| XD | Advanced Liver Disease | 0.54999 |
| XE | AIDS | 31.9221 |
| XF | Allergic Rhinitis | 10.1509 |
| XG | Amyotrophic Lateral Schlerosis (Lou Gehrig's disease) | 29.0981 |
| XH | Alzheimer's Disease | 6.54956 |
| XI | Angina/Coronary Artery Disease | 0.067019 |
| XJ | Anxiety Disorder/Panic Disorder/Social Phobia | 3.17593 |
| XK | Arrythmia | 6.09765 |
| XL | Asthma (under 55) | 9.0274 |
| XM | Benign Prostatic Hyperplasia | 7.97429 |
| XN | Cancer (any type) | 10.8211 |
| XO | Congestive Heart Failure | 2.18044 |
| XP | Chronic Obstructive Pulmonary Disease(55+) | 3.57019 |
| XQ | Cystic Fibrosis | 5.16423 |
| XR | Depression | 10.3768 |
| XS | Diabetes Type I - Insulin dependent | 9.019 |
| XT | Diabetes Type II - Non-Insulin dependent | 7.29497 |
| XU | End Stage Renal Disease (ESRD) | 12.5402 |
| XV | Epilepsy | 6.93106 |
| XW | Gaucher's Disease | 83.2477 |
| XX | Glaucoma | 2.31705 |
| XY | Gout | 1.98149 |
| XZ | Growth Hormone Deficiency | 32.512 |
| XAA | Hepatitis B | 4.09929 |
| XBB | Hepatitis C | 33.2874 |
| XCC | High Cholesterol/Triglycerides | 10.7383 |
| XDD | Hypertension | 8.30913 |
| XEE | Hypothyroidism | 1.21422 |
| XFF | Inflammatory Bowel Disease | 8.56743 |
| XGG | Manic Depressive | 4.62228 |
| XHH | Migraine | 8.26695 |
| XLL | Multiple Sclerosis | 30.5853 |
| XMM | Organ Transplantation | 17.0153 |
| XNN | Menopause (Hormone Replacement Therapy) (45-59) | 7.26419 |
| XOO1 | Osteoporosis (Bone Resorption Suppression Agents) (60+) | 6.69366 |
| XOO2 | Osteoporosis (Estrogenic Agents) (60+) | 3.50463 |
| XPP | Parkinson's Disease | 8.11787 |
| XQQ | Peripheral Vascular Disease | 1.76236 |
| XRR | Psoriasis | 9.92265 |
| XSS | Psychotic Disorders/Dementia and no antidepressants (65+) | 4.5396 |
| XTT | Rheumatoid Arthritis | 10.5781 |
| XUU | Schizophrenia (under 65) | 13.8768 |
| XVV | Smoking Cessation | 3.40704 |
| XWW | Thromboembolytic Disease I (Platelet Aggregation Inhibitors) | 1.44029 |
| XKK | Thromboembolytic Disease II (Oral Anticoagulants, Coumarin Type) | 2.83761 |
| XYY | Tuberculosis | 5.049 |
| XZZ | Urinary Incontinence | 3.66661 |

The weights are then, for example, multiplied by the indicator variables (e.g., "1" for "TRUE" or the presence of the chronic condition and "0" for "FALSE" or the absence of the chronic condition) and, for example, summed to get a chronic conditions score. Furthermore, an indicator for patients with no pharmacy claims (e.g., a "no-claim" weight) may optionally be considered (set to a value of 1 for members with no pharmacy claims and 0 otherwise, which is multiplied by a no-claims weight) to further modify the chronic conditions score. Thus, this no-claim weight further emphasizes situations where an individual has no pharmacy claims whatsoever (i.e., the patient has no chronic condition claims, prescribed medications and/or other claims).

The pharmacy claims are also reviewed to determine compliance on certain pharmaceuticals of interest. In one embodiment, compliance is defined as the total days of supply over a year (e.g., the days supply divided by 365 times 100%). In other embodiments, other time periods are used (e.g., 7 days, 30 days, etc.). Two sets of weights, one from a log transform (or log index) and one from a square-root transform (or square-root index) are included in Table II (shown below), for each medication, for use in generating a compliance medication score. Either weight may be used. When the weights are developed in practice, in some cases, whichever transform minimizes the multiple regression model's error sum of squares may be most appropriate. The weights are multiplied by the indicator or numeric variables (i.e., the days supply or compliance) and summed to generate the medication compliance score. Table II, below, provides exemplary indices (the generation of which is described in greater detail below) for a number of compliance medications.

TABLE II

| Compliance Medication | Weights for log index | Weights for square root index |
|---|---|---|
| Chronic Condition Score | 0.08036 | 0.65876 |
| No Claim | −2.24249 | −5.42877 |
| Asthma Medications | 0.00734 | 0.07566 |
| Asthma Controllers | 0.00246 | 0.06420 |
| Congestive Heart Failure Medications | −0.00095396 | 0.00615 |
| Angiotension Converting Enzymes | 0.00183 | 0.00987 |
| Gastrointestinal Medications | −0.00041974 | 0.04681 |
| Proton Pump Inhibitors | 0.00490 | 0.07727 |
| High Cholesterol Medications | 0.00020414 | 0.01141 |
| Statins | 0.00339 | 0.04491 |
| Diabetes Medications | −0.00010360 | 0.07623 |
| Diabetes Type 2 Medications | 0.00285 | 0.06342 |
| Depression Medications | 0.00358 | 0.07158 |
| Hypertension Medications | 0.00811 | 0.04302 |

Once generated, the medical compliance score and the chronic conditions score are summed to produce the risk index of the present invention, which (as mentioned above) may be used to predict future medical costs, total healthcare costs, and probability and amounts of future medical services utilization. Specifically, an individual with a higher score will likely have more comorbidities, and hence represent a more expensive patient, than an individual with a lower score. Thus, the risk indices of the individuals in a particular population may be compared, with higher scores indicating a high risk of pharmaceutical cost and risk of future total medical cost and medical utilization.

In at least one embodiment, the index is generated by first examining the individual's pharmacy claims to identify any predetermined conditions, such as chronic conditions possessed by the individual. Similarly, the individual's pharmacy claims are examined to identify any compliance medications prescribed to the individual. The chronic condition information is used, for example, to generate a chronic condition score by summing regression coefficients for each chronic condition possessed by the individual. Likewise, the compliance medication information is used, for example, to generate a compliance medication score by, for example, summing products of regression coefficients for each compliance medication prescribed to the individual with associated medication supply weights. From there, a modified chronic condition score is generated by, for example, multiplying the chronic condition score by a chronic condition regression coefficient. The modified chronic condition score may then be further modified by, for example, subtracting a no-claims weight from the chronic condition score in cases where the individual has no pharmacy claims. Finally, the risk index may be determined by, for example, summing the modified chronic condition score and the compliance medication score.

Other embodiments of the present invention also provide a method, system, and computer-readable instructions for generating a risk index for an individual using the individual's pharmacy claims. In these alternate embodiments, the index is generated by first generating a raw risk index indicative of at least one of the individual's raw relative medical costs, acute medical conditions, and variation in medical costs, by using the individual's pharmacy claims. Next, the raw risk index is modified in accordance with a compliance medication score, which is indicative of the individual's compliance with prescribed pharmaceuticals. Summing the above values results in the risk index of this embodiment of the present invention.

In yet other cases, other embodiments of the present invention provide method, system, and computer-readable instructions for generating a risk index for an individual using the individual's pharmacy claims and a no-claims weight. In these alternate embodiments, the index is generated by first generating a raw risk index indicative of at least one of the individual's raw relative medical costs, acute medical conditions, and variation in medical costs, by using the individual's pharmacy claims. Subsequently, the raw risk index is modified in accordance with a no-claims weight, which is indicative of an absence of claims in the individual's pharmacy claims. Like the above, summing these values results in the risk index of this embodiment of the present invention.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE SEVERAL VIEWS OF THE DRAWING(S)

The above-mentioned and other advantages and features of the present invention will be better understood from the following detailed description of the invention with reference to the accompanying drawings, in which.

Figure 8:
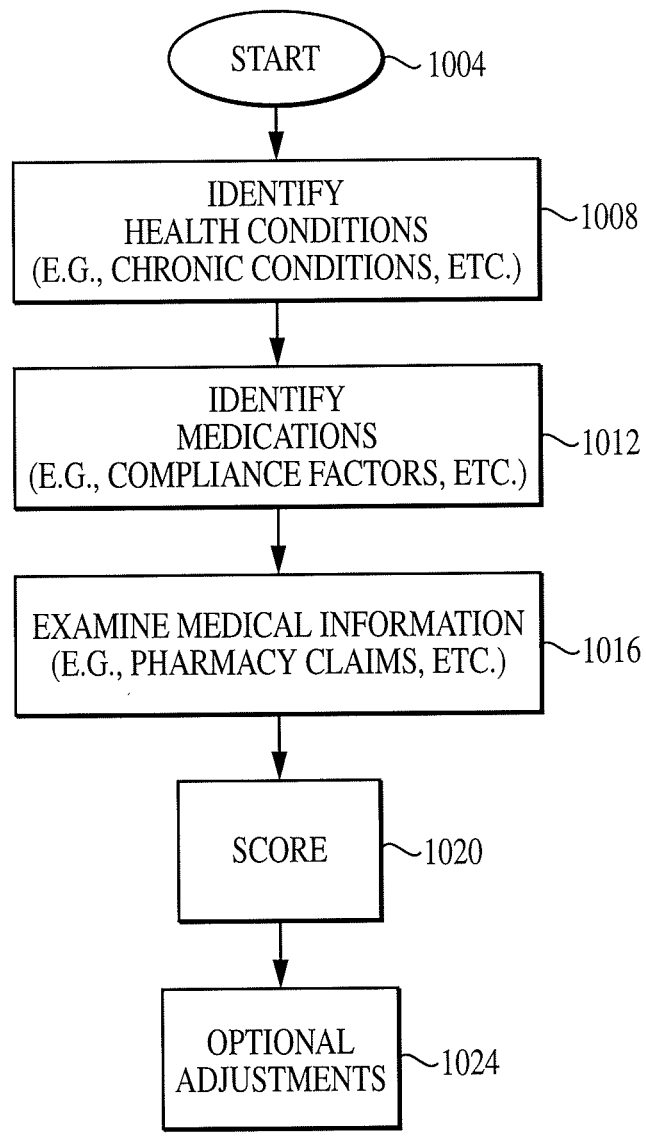
Figure 9:
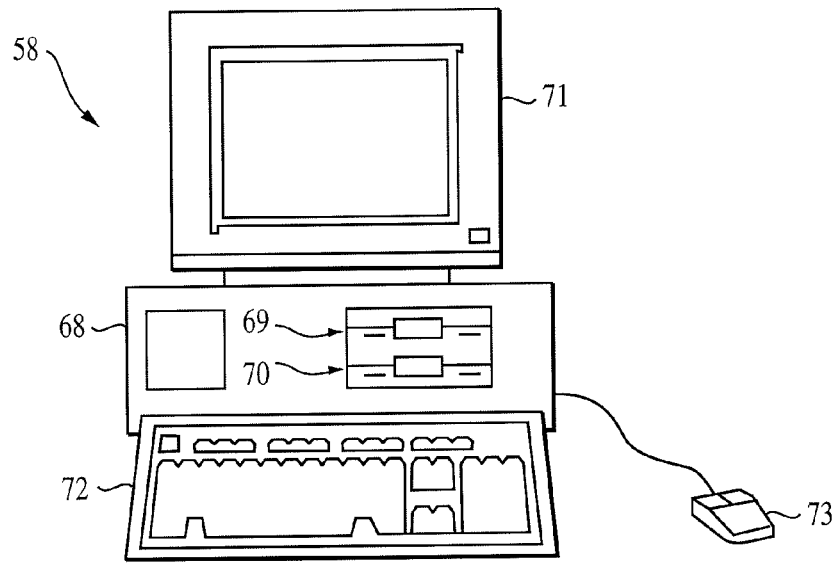
Figure 10:
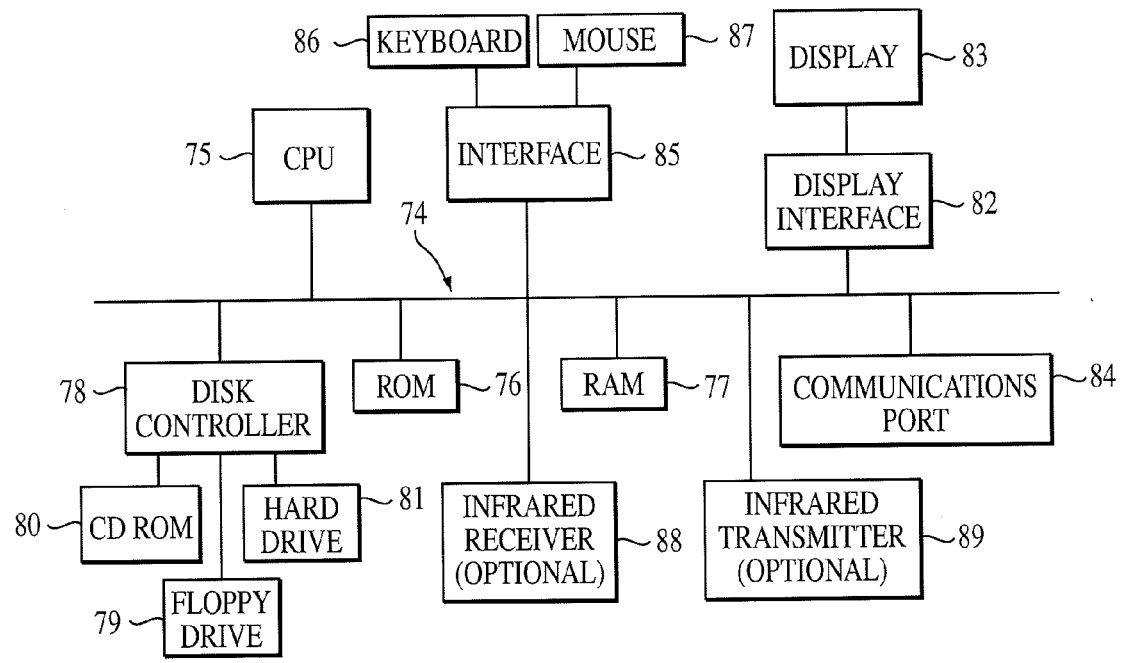
Figure 11:
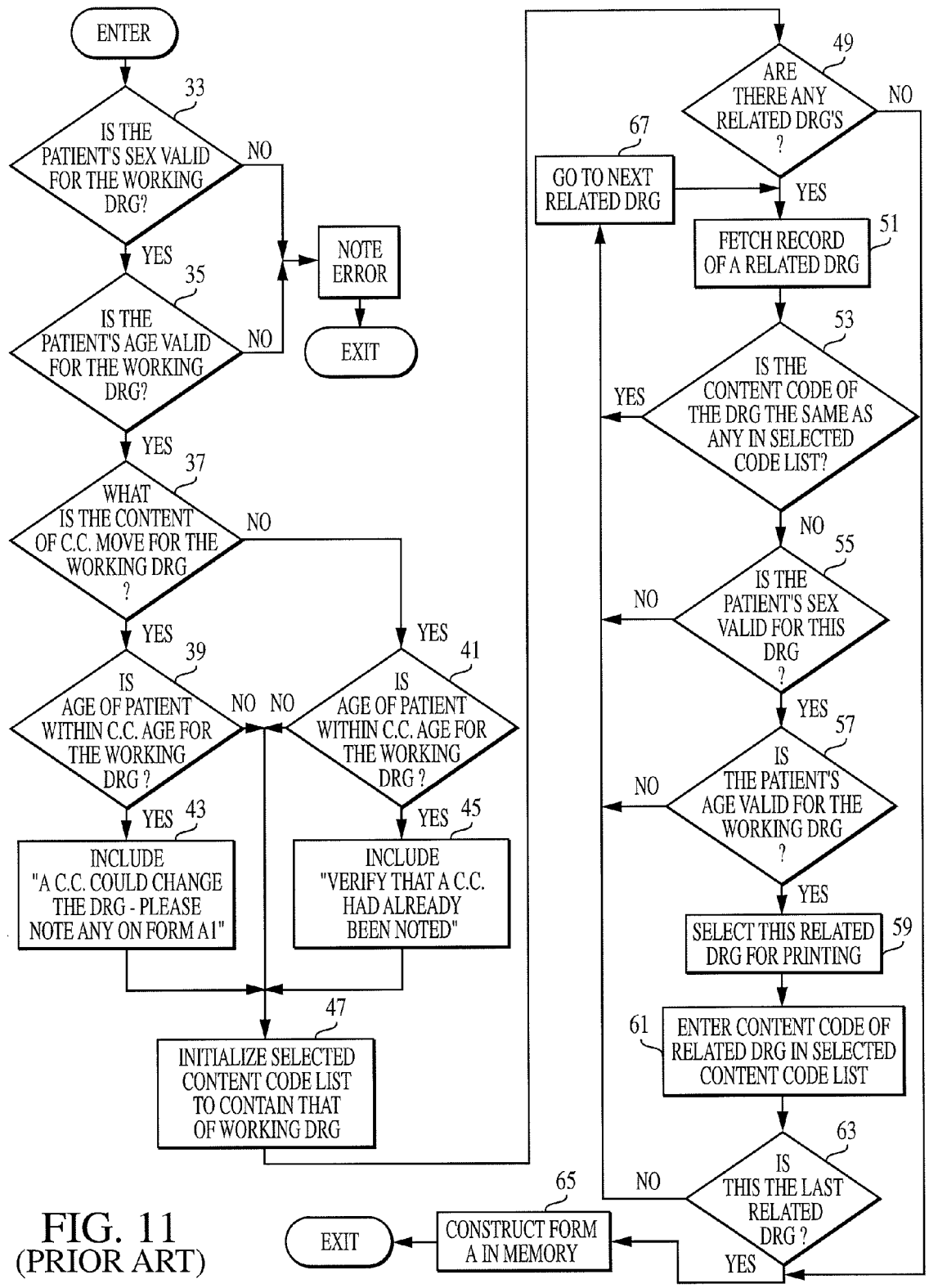

FIG. 6 lists examples of chronic conditions and associated regression coefficients utilizable in generating the risk index of the present invention;

FIG. 7 lists examples of compliance medications and associated regression coefficients utilizable in generating the risk index of the present invention;

FIG. 8 is an example of yet another embodiment of a process utilizable for generating a risk index according to the techniques of the present invention;

FIG. 9 is a block diagram example of a computer utilizable for generating the risk index of the present invention;

FIG. 10 illustrates a block diagram of the internal hardware of the computer of FIG. 9; and FIG. 11 depicts a prior art method used to implement a medical reimbursement computer program.

DETAILED DESCRIPTION OF THE INVENTION

The following detailed description includes many specific details. The inclusion of such details is for the purpose of illustration only and should not be understood to limit the invention. Throughout this discussion, similar elements are referred to by similar numbers in the various figures for ease of reference. In addition, features in one embodiment may be combined with features in other embodiments of the invention.

Specifically, a healthcare risk index is generated using, for example, information from a patient or individual's pharmacy claims, which are indicative of, for example, chronic conditions possessed by the individual, the individual's compliance on certain medications, and situations where the individual has no claims whatsoever. The index may be used to explain and predict variation in pharmacy-related costs and variation in total healthcare costs or utilization. In particular, the index is generated, for example, by first examining the individual's pharmacy claims to identify any chronic conditions possessed by the individual. Similarly, the individual's pharmacy claims are examined to identify, for example, any compliance medications prescribed to the individual. The chronic condition information is used, for example, to generate a chronic condition score by summing regression coefficients for each chronic condition possessed by the individual. Likewise, the compliance medication information is used, for example, to generate a compliance medication score by summing products of regression coefficients for each compliance medication prescribed to the individual with associated medication supply weights. From there, a modified chronic condition score is generated by, for example, multiplying the chronic condition score by a chronic condition regression coefficient. The modified chronic condition score may then be further modified by, for example, subtracting a no-claims weight from the chronic condition score in cases where the individual has no pharmacy claims. Finally, the risk index may be determined, for example, by summing the modified chronic condition score and the compliance medication score.

Figure 1:
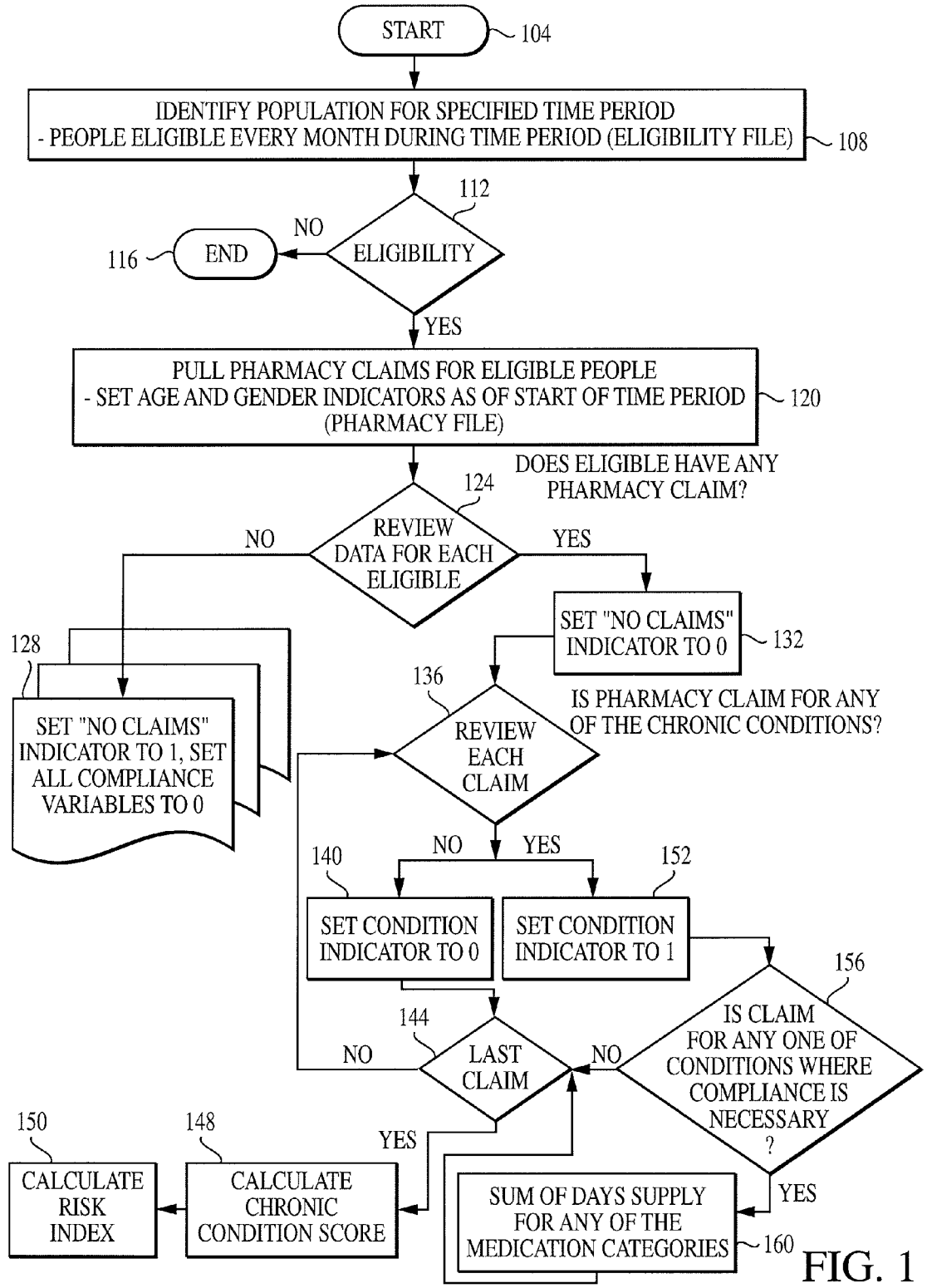
FIG. 1 is one example of a process utilizable for generating a chronic condition score and a compliance medication score for use in generating a risk index according to the techniques of the present invention.

Referring first to FIG. 1, one example of a process utilizable for generating a chronic condition score and a compliance medication score used to generate a risk index according to the techniques of the present invention is illustrated. As will be discussed in greater detail below, these scores may be utilized to generate a risk score or risk index of the present invention. More specifically, the risk index of the present invention represents a "burden of illness" score, which when compared to other scores, may be used to predict relative healthcare costs. In at least some embodiments, higher scores imply more comorbidities, and hence represent more expensive relative illnesses. The index allows for accurate comparisons between various populations by adjusting for a "burden of illness." In addition, the index may be used to predict future medical costs, total healthcare costs, and probability and amounts of future medical services utilization.

In accordance with the concepts of the present invention, numerous factors may affect the risk index. Specifically, the scores may increase according to the number of diseases present, but generally not according to the number of prescriptions within a category. Similarly, more costly diseases may receive higher scores. In at least some embodiments of the present invention, the index specifically considers a patient's compliance with certain medications, as well as situations where a patient has no pharmacy claims whatsoever (i.e., the patient received no prescriptions).

The generation of the risk index commences (STEP 104) with the determination of an eligible population for a specified period of time (STEP 108). To perform this step, the process may examine the contents of an eligibility file. In most cases, the eligibility file includes a database containing a list of each of the eligible individuals, maintained by a managed care organization, a pharmacy benefits manager, a human resources department of an employer, or other similar organization. For example, the eligible individuals may include each of those employees of a particular employer that have elected to receive healthcare benefits from the employer. In contrast, individuals that have elected not to receive healthcare benefits from the employer constitute ineligible individuals.

Thus, the process examines each entry or individual for eligibility (STEP 112). For each ineligible individual, processing terminates (STEP 116), with no risk score being generated for that individual. For those that are eligible, pharmacy claims information for the individuals is examined (STEP 120).

Specifically, a pharmacy file, which is used to maintain the medical history data for each of the individuals, is retrieved and subsequently consulted. In addition to the patient's name, gender, age, and other personal information, this file includes information describing each prescription filled under a benefit offer by the employer. This includes pharmaceuticals filled from outpatient pharmacies, retail claims, mail order prescription claims, or other similar claims, but excludes medications sold over-the-counter. Hence, the information in the pharmacy file necessarily identifies, for example, a chronic condition possessed by each individual (if any), as well as the individuals' compliance with the medication, which may be defined as the number of days supply of medication coverage for the time period divided by the number of days in the time period multiplied by 100%, and the like. Any time periods are possible, include, for example, 365 days, 7 days, etc.

Once the pharmacy claims information for the eligible individuals has been retrieved, the data for each individual is reviewed (STEP 124). Specifically, the process first identifies whether each individual has any pharmacy claims. As part of this procedure, the process identifies those individuals that have no pharmacy claims whatsoever.

In accordance with the concepts of the present invention, individuals with no claims are at the lowest risk for adverse events and utilization for costs. As a result, the scores associated with these individuals are modified in accordance with a "no-claims" weight or modifier (discussed in greater detail below). Thus, in the example illustrated in FIG. 1, no-claims indicators associated with these individuals are set (STEP 128). For example, an indicator may be set to "1" or "TRUE" if the individual has no claims. Correspondingly, compliance variables for these individuals (i.e., indicators relating to a patient's compliance with medications) are set to indicate that there was no use of medications.

As discussed above, with individuals determined to have at least one claim (as determined in STEP 124), the no claims indicator is set (STEP 132). For example, an indicator may be set to "0" or "FALSE" if the individual has no claims. Subsequently, the pharmacy claims data for each of these individuals is examined to identify the presence or absence of a chronic condition of interest (STEP 136).

More specifically, the pharmacy claims are searched for prescribed medications used to treat any of a predetermined number of chronic conditions or diseases. In the example illustrated in FIG. 1, the chronic conditions listed in FIG. 6 may be utilized. Thus, the process in FIG. 1 identifies the presence (or absence) of each of those chronic conditions for each individual. Furthermore, although specific chronic conditions are provided in FIG. 6, it should be noted that these conditions are listed for exemplary purposes only, and that numerous other conditions may just as easily be considered. Specifically, the exact combination of chronic conditions may be determined by the administrator or user of the system (see e.g., the embodiment of FIG. 5).

If the process determines that an individual possesses one of the predetermined chronic conditions of interest, an indicator corresponding to that condition is set to "1" or to a "TRUE" state (STEP 152). If, on the other hand, the process determines that the individual does not possess the predetermined chronic condition of interest, the indicator corresponding to that condition is set to "0" or to a "FALSE" state (STEP 140).

In addition to the presence or the absence of a chronic condition, the present invention also considers a patient or individual's compliance on the medications used to treat certain chronic conditions. More specifically, an individual's compliance measures whether that patient's illness is being treated properly. As will be discussed in greater detail below, one embodiment of the present invention measures compliance according to the amount or supply of a medication prescribed to a patient (for a specified period of time). Thus, whereas a chronic condition score is used to measure the presence or absence of certain chronic conditions, a compliance medication score is used to measure an individual's compliance with a medication.

To illustrate, asthma is a measurable chronic condition. As such its presence (or absence) may be measured using an asthma chronic condition score. In addition, asthma may typically be treated using asthma controller medications. Compliance with this medication may therefore also be measured, specifically, using an asthma medication compliance score. The present invention considers these factors because, for example, an asthmatic patient who does not use his or her medication properly may be at a higher risk for an adverse event than a patient who is asthmatic but has a high compliance with controller medications (and is therefore at a lower risk).

Thus, the process searches the pharmacy claims for the presence of any conditions where medication compliance is to be considered (STEP 156). In the example illustrated in FIG. 1, the medications listed in FIG. 7 may be utilized. Furthermore, although specific medications are provided in FIG. 7, it should be noted that these medications are listed for exemplary purposes only, and that numerous other medications may just as easily be considered. Specifically, the exact combination of compliance medications may be determined by the administrator or user of the system (see e.g., the embodiment of FIG. 5).

Once the compliance medications have been determined (STEP 156), a compliance medication score for each medication is generated (STEP 160). In the example illustrated in FIG. 1, this score is generated by summing the days supply for each medication, dividing by a predetermined number of days (e.g., 365 days, 1 week, etc.), and multiplying by 100%.

Thus, the above described process continues with an analysis of each pharmacy claim of interest (STEP 136) and an analysis of any desired conditions for medication compliance (STEP 156) until each claim has been examined (STEP 144). From there, the above-generated information is utilized to generate a chronic condition score (STEP 148). Specifically, for each chronic condition possessed by an individual, a weight associated with the condition is added to the chronic condition score. As an example, the weights listed in the table of FIG. 6 may be used. Thus, a chronic condition score associated with a patient diagnosed with cancer is increased by the weight associated with cancer, which in this case is 10.8211. Similarly, if that same patient also smokes, the chronic condition score is increased by 3.40704. The sum total of these chronic condition weights thereby constitutes the chronic condition score of an individual (or i.e., a raw chronic condition score in embodiments where modifications or the absence of pharmacy claims are considered).

The weights associated with the chronic conditions are generated using information contained in a pharmacy claims database. Specifically, each weight represents the regression coefficient developed using a multiple regression model with pharmaceutical or total cost as the dependent variable and all chronic conditions of interest as independent variables. The coefficients shown in the example of FIG. 6 were determined using data from a pharmaceutical benefits manager database (one example of which includes Medco Health Solutions pharmacy claims database). Other data sources (such as other health insurers, PBMs containing pharmacy claims, etc.) may just as easily be utilized by those of ordinary skill in the art to calculate these regression coefficients. After generating the chronic condition score, a risk index is calculated (STEP 150).

Figure 2:
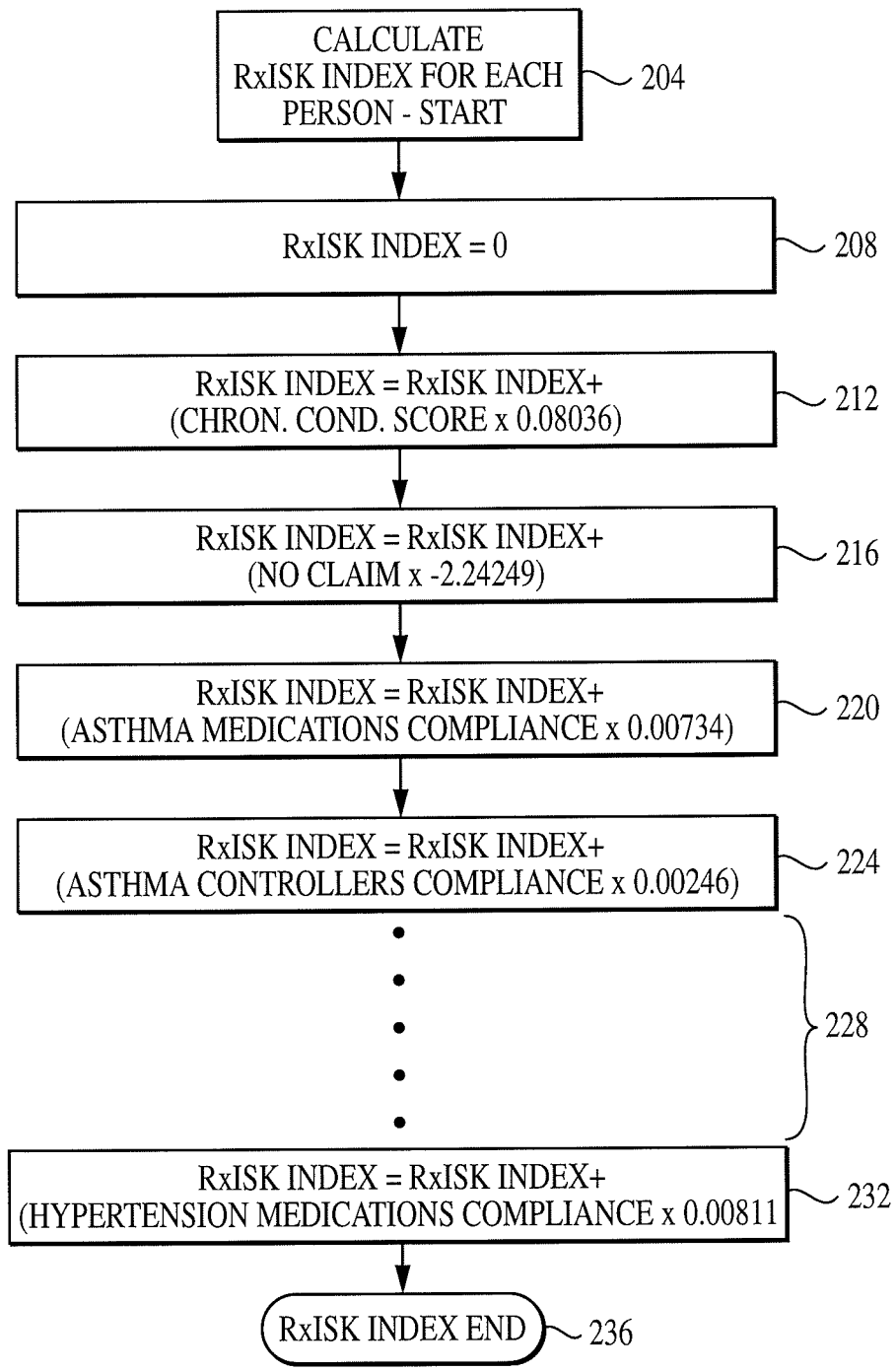
FIG. 2 is one example of a portion of a process utilizable for generating a risk index according to the techniques of the present invention.

Referring now to FIG. 2, one example of a portion of a process utilizable for generating a risk index is now described. As mentioned above, the risk index of the present invention advantageously incorporates any number of factors including, for example, the number and types of chronic conditions and diseases, modifications for variance, modifications for patients with no pharmacy claims, and the level of compliance with any number of prescribed medications.

The risk index calculation starts (STEP 204) by initializing the index, in this example, to zero (STEP 208). As discussed above, the index may be adjusted according to the number and types of chronic conditions possessed by an individual. As discussed above with reference to STEP 148 of FIG. 1, for each chronic condition possessed, the risk index may be modified by a weight associated with the condition.

Once the chronic condition weights have been summed, the total may optionally be modified according to a regression coefficient relating to the entire or overall chronic condition score (STEP 212). In the example in FIG. 2, the sum of the chronic condition weights is multiplied by an overall regression coefficient.

In accordance with the concepts of the present invention, a modification may also be made for patients with no pharmaceutical claims (STEP 216). Specifically, in the example of FIG. 2, the indices associated with individuals with no pharmaceutical claims whatsoever are modified according to a no-claim weight. For instance, as depicted in FIG. 2, the regression coefficient for the no-claim indicator (e.g., 2.24249) is subtracted from the chronic condition score. An example of a no-claims weight calculated using data from a pharmacy claims database (one example of which includes Medco Health Solutions' pharmacy claims database) is shown in FIG. 7.

Although the example of FIG. 2 shows the no claim weight being subtracted from the chronic condition score, it is to be understood that modifications (including the no claim weight and others) may be made to any component of the risk index and at any time during the process. For example, the no claim weight may just as easily be applied as a fraction to be multiplied against the compliance medication score (described below).

In addition to the chronic condition score and other modifiers (e.g., the no-claim and variance modifiers), a compliance medication component is also considered in the generation of the risk index. Specifically, each medication to be considered for compliance is associated with a regression coefficient for that medication (see the examples listed in FIG. 7). To generate the compliance medication score, the number of days supply divided by the number of days in the time period multiplied by 100% (i.e., a compliance) for each medication is multiplied against the compliance medication's regression coefficient.

Thus, in the example of FIG. 2, the compliance for asthma medications is multiplied by 0.00734 (STEP 220); the compliance for asthma controllers is multiplied by 0.00246 (STEP 224); and the compliance for hypertension medications is multiplied by 0.00811 (STEP 232). Other compliance medications of interest are addressed in a similar manner (STEP 228).

Once these individual compliance medication scores have been generated, they are summed and added to the risk index, thereby completing the risk index generation process (STEP 236).

Although specific regression coefficients were provided in the example of FIG. 2 above (i.e., based on data obtained from, e.g., the Medco Health Solutions pharmacy claims database), it is to be understood that these values were provided for exemplary purposes only. Specifically, those of ordinary skill in the art will recognize that each distinct data source would result in the generation of alternative regression coefficients.

Figure 3:
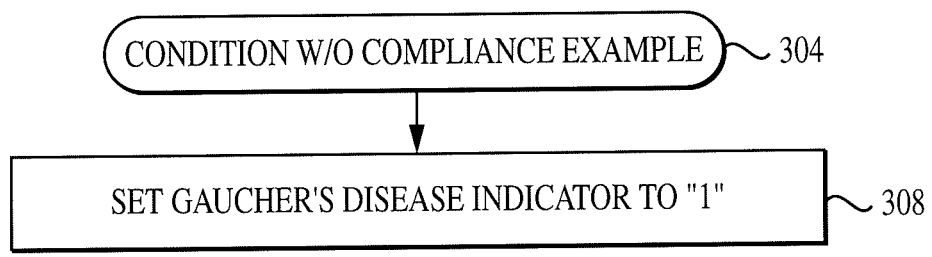
FIG. 3 illustrates one example of the generation of the risk index of the present invention without a compliance medication component.

FIG. 3 illustrates one example of the generation of a portion of the risk index of the present invention without a compliance medication component. In this example, processing starts (STEP 304) with an identification of all chronic conditions of interest from, e.g., a pharmacy claims database. Here, the process identifies the existence of Gaucher's Disease. Thus, the process sets a Gaucher's Disease indicator to 1 or TRUE (STEP 308). This indicator is then multiplied by the regression coefficient for Gaucher's Disease (i.e., 83.2477 in the example of FIG. 6) to produce a weight (e.g., 83.2477), which is added to the patient's risk index.

Figure 4:
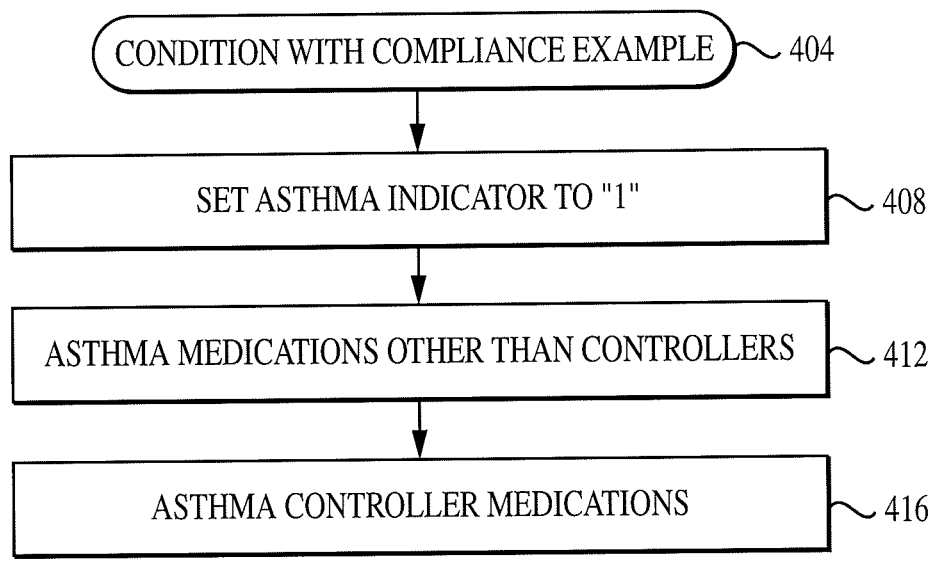
FIG. 4 illustrates one example of the generation of the risk index of the present invention with a compliance medication component.

FIG. 4 illustrates one example of the generation of a portion of the risk index of the present invention with a compliance medication component. The process commences (STEP 404) with an identification of all chronic conditions of interest from, e.g., a pharmacy claims database. Here, the process identifies the existence of asthma. Thus, the process sets an asthma indicator to 1 or TRUE (STEP 408). This indicator is multiplied by the regression coefficient for asthma (i.e., 9.0274 in the example of FIG. 6) to produce a weight (e.g., 9.0274), which is added to the patient's risk index.

Referring again to FIG. 4, because the medications used to treat asthma are also of interest in this example, the process continues by checking the patient's compliance with asthma medications and controllers. Thus, the process sums the days supply for asthma medications other than controllers (STEP 412) while at the same time summing the days supply for asthma controllers (STEP 416). These values are converted to compliance measures by dividing by the number of days in the time period and multiplying by 100%. These compliance measures are later multiplied by the regression coefficient for asthma medications (other than controllers) (i.e., 0.0734 in the example of FIG. 7) and by the regression coefficient for asthma controllers (i.e., 0.00246 in the example of FIG. 7), respectively. Assuming a time period of 365 days and a 150 day supply of asthma medication for an asthma medication compliance of 41% (i.e., 150/365×100%) and a 365 day supply of asthma controllers for an asthma controller compliance of 100%, the risk index is increased by 0.0326 (i.e., 41%×0.0734+100%×0.00246).

Figure 5:
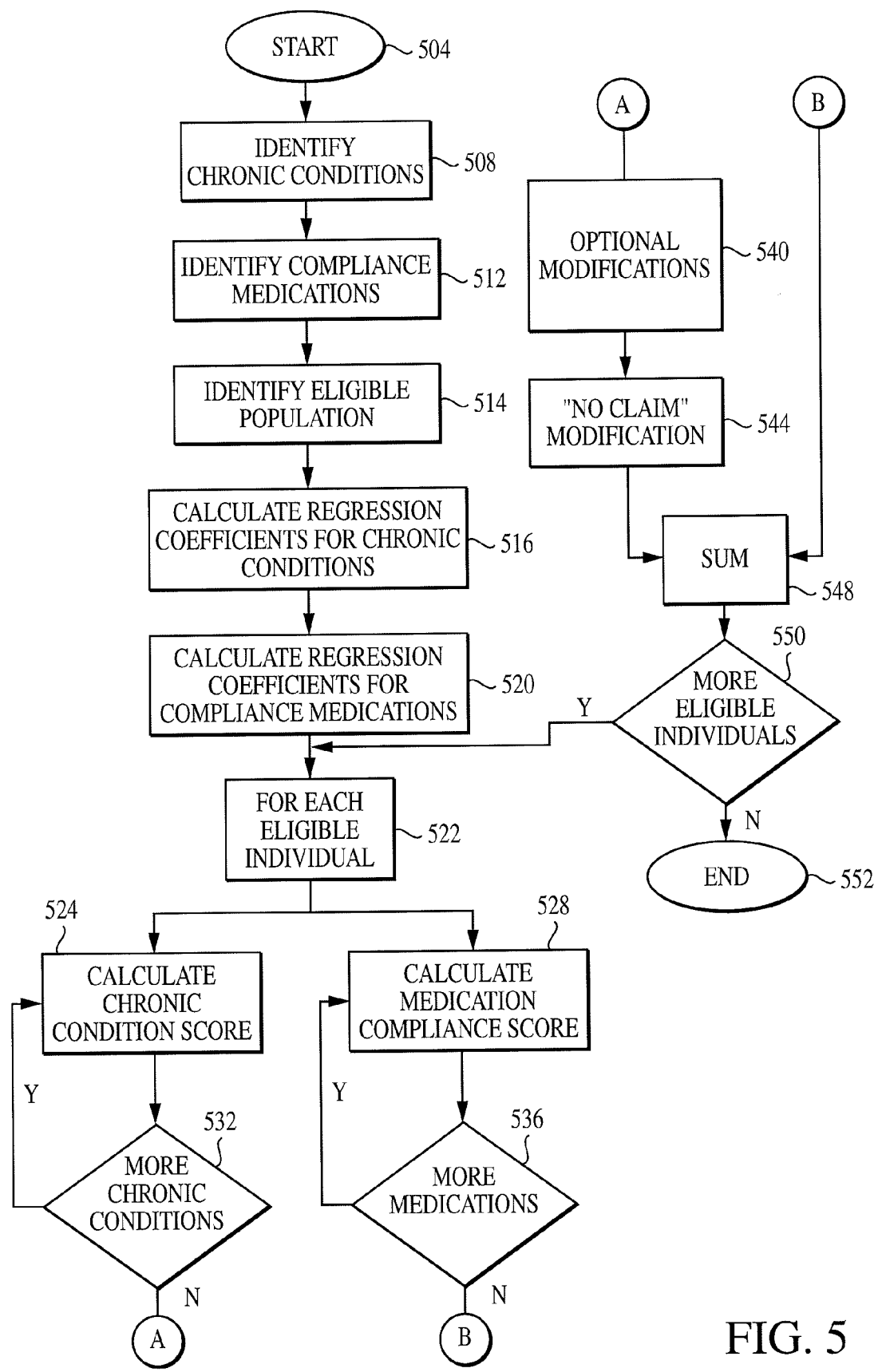
FIG. 5 is an example of another embodiment of a process utilizable for generating a risk index according to the techniques of the present invention.

FIG. 5 is an example of another embodiment of a process utilizable for generating the risk index of the present invention. The process starts (STEP 504) with an identification of the chronic conditions to be considered in generating the present risk index (STEP 508). For example, a query may be made to a process administrator or user for the chronic conditions of interest. Any chronic conditions may be utilized in addition to the conditions listed in FIG. 6.

Once the chronic conditions of interest have been determined, the compliance medications of interest are determined (STEP 512). Like with the identification of chronic conditions, a user may be asked to input the compliance medications of interest. Similarly, the information may be downloaded from a file or other data source.

Once the conditions and medications of interest have been identified, an eligible population for a specified period of time is determined (STEP 514). To perform this step, the process may examine a database maintained by a managed care organization, a pharmacy benefits manager, a human resources department of an employer, or other similar organization, and identify each of the individuals that are eligible for participation in a benefits plan (i.e., individuals that have elected to receive healthcare benefits from an employer).

For those individuals that are eligible, regression coefficients for their chronic conditions and compliance medications are calculated. To calculate the regression coefficients, as known to those of ordinary skill in the art, a multiple regression model is run using the pharmacy or total cost for each patient as the dependent variable and including an independent variable for each condition and medication of interest for each patient. The model is run on the data using statistical software which outputs the estimates of the regression coefficients based on the fit of the model to the data. For example, the regression coefficients for each of the chronic conditions of interest may be calculated by running a multiple regression model using pharmacy or total costs for each patient as the dependent variable and including an independent variable for each condition of interest for each patient. The model is run on the data using statistical software which outputs the estimates of the regression coefficients based on the fit of the model to the data (STEP 516). Similarly, the regression coefficients for each of the compliance medications of interest may be calculated by running a multiple regression model using pharmacy or total cost for each patient as the dependent variable and including an independent variable for each compliance medication of interest from a pharmaceutical benefits manager database (such as e.g., the Medco Health Solutions database) for each patient. The model is run on the data using statistical software which outputs the estimates of the regression coefficients based on the fit of the model to the data (STEP 520).

Subsequently, a raw or unmodified chronic condition score may be generated by summing the regression coefficients of each of the chronic conditions possessed by the individuals or patients (STEP 524). As discussed above, the presence or absence of a condition may be determined by examining the pharmacy claims for each individual. This process continues until each individual has been checked for each chronic condition (STEP 532).

In accordance with the concepts of the present invention, the raw chronic condition score may be modified according to a regression coefficient relating to the entire or overall chronic condition score (STEP 540). Similarly, a no-claim modification may be made to account for individuals that possess no pharmacy claims whatsoever (STEP 544). More particularly, a no-claims weight may be subtracted from the score. These modifications may be made to produce a modified or final chronic condition score.

In conjunction with the calculation of the chronic condition score, a compliance medication score may be generated by multiplying the compliance of prescribed medication against an associated regression coefficient for each of the compliance medications possessed by the individuals or patients (STEP 528). As discussed above, the compliance medications prescribed to an individual, and the compliance thereof, may be determined by examining the pharmacy claims for each individual. This process continues until each individual has been checked for each compliance medication (STEP 536).

From there, the modified chronic condition score may be added to the compliance medication score to result in the risk index of the present invention (STEP 548). The above process continues, repeating STEPS 524, 528, 532, 536, 540, 544, and 548 for the eligible individuals of the population (STEP 550), until a risk index has been generated for each (STEP 552).

Furthermore, although each of the examples above describes the use of pharmacy claims information in the generation of the risk index of the present invention, it is to be understood that factors in addition to or in place of pharmacy claims information may be utilized. For example, alternate embodiments of the present invention contemplate using analogous and/or other similar information such as medical information in place thereof.

FIG. 8 is an example of yet another embodiment of a process utilizable for generating the risk index of the present invention. The process starts (STEP 1004) with an identification of any health conditions to be considered in generating the present risk index (STEP 1008). As an example, this may include any chronic conditions of interest, although other conditions are possible.

Once the health conditions have been determined, the medications of interest are identified (STEP 1012). As an example, this may include any compliance medications of interest, although other medications are possible.

From there, medical information for each individual is examined to calculate regression coefficients for each health condition and medication associated with each individual. For example, the methods described above (e.g., the procedures described in FIGS. 1-5 above) may be used. Subsequently, these results may be summed (STEP 1016) to generate a raw score for each individual (STEP 1020).

Once the raw scores have been generated for each individual, they may optionally be modified (STEP 1024) to consider, for example, individuals with no claims and/or other factors (see, e.g., STEPS 540 and 544 of FIG. 5 above), to result in the risk index of the present invention.

The risk index generation process of the present invention may be implemented in any computer system or computer-based controller. One example of such a system is described in greater detail below with reference to FIG. 9. More specifically, FIG. 9 is an illustration of a computer 58 used for implementing the computer processing in accordance with a computer-implemented embodiment of the present invention. The procedures described above may be presented in terms of program procedures executed on, for example, a computer or network of computers, including local and/or global area networks such as the Internet.

Viewed externally in FIG. 9, computer 58 has a central processing unit (CPU) 68 having disk drives 69, 70. Disk drives 69, 70 are merely symbolic of a number of disk drives that might be accommodated by computer 58. Typically, these might be one or more of the following: a floppy disk drive 69, a hard disk drive (not shown), and a CD ROM or digital video disk, as indicated by the slot at 70. The number and type of drives varies, typically with different computer configurations. Disk drives 69, 70 are, in fact, options, and for space considerations, may be omitted from the computer system used in conjunction with the processes described herein.

Computer 58 also has a display 71 upon which information may be displayed. The display is optional for the computer used in conjunction with the system described herein. A keyboard 72 and/or a pointing device 73, such as a mouse 73, may be provided as input devices to interface with central processing unit 68. To increase input efficiency, keyboard 72 may be supplemented or replaced with a scanner, card reader, or other data input device. The pointing device 73 may be a mouse, touch pad control device, track ball device, or any other type of pointing device.

Alternatively, referring to FIG. 10, computer 58 may also include a CD ROM reader and writer 80, which are interconnected by a bus 74 along with other peripheral devices supported by the bus structure and protocol. Bus 74 serves as the main information highway interconnecting other components of the computer.

FIG. 10 illustrates a block diagram of the internal hardware of the computer of FIG. 9. CPU 75 is the central processing unit of the system, performing calculations and logic operations required to execute a program. Read only memory (ROM) 76 and random access memory (RAM) 77 constitute the main memory of the computer. Disk controller 78 interfaces one or more disk drives to the system bus 74. These disk drives may be floppy disk drives such as 79, or CD ROM or DVD (digital video/versatile disk) drives, as at 80, or internal or external hard drives 81. As previously indicated these various disk drives and disk controllers are optional devices.

A display interface 82 permits information from bus 74 to be displayed on the display 83. Again, as indicated, the display 83 is an optional accessory for a central or remote computer in the communication network, as are infrared receiver 88 and transmitter 89. Communication with external devices occurs using communications port 84.

In addition to the standard components of the computer, the computer may also include an interface 85, which allows for data input through the keyboard 86 or pointing device, such as a mouse 87.

The foregoing detailed description includes many specific details. The inclusion of such detail is for the purpose of illustration only and should not be understood to limit the invention. In addition, features in one embodiment may be combined with features in other embodiments of the invention. Various changes may be made without departing from the scope of the invention as defined in the following claims.

As another example, the system according to the invention may include a general purpose computer, or a specially programmed special purpose computer. The user may interact with the system via e.g., a personal computer or over PDA, e.g., the Internet an Intranet, etc. Either of these may be implemented as a distributed computer system rather than a single computer. Similarly, the communications link may be a dedicated link, a modem over a POTS line, and/or any other method of communicating between computers and/or users. Moreover, the processing could be controlled by a software program on one or more computer systems or processors, or could even be partially or wholly implemented in hardware.

Although the computer system in FIG. 9 is illustrated as having a single computer, the system according to one or more embodiments of the invention is optionally suitably equipped with a multitude or combination of processors or storage devices. For example, the computer may be replaced by, or combined with, any suitable processing system operative in accordance with the concepts of embodiments of the present invention, including sophisticated calculators, hand held, laptop/notebook, mini, mainframe and super computers, as well as processing system network combinations of the same. Further, portions of the system may be provided in any appropriate electronic format, including, for example, provided over a communication line as electronic signals, provided on floppy disk, provided on CD Rom, provided on optical disk memory, etc.

Any presently available or future developed computer software language and/or hardware components can be employed in such embodiments of the present invention. For example, at least some of the functionality mentioned above could be implemented using Visual Basic, C, C++ or any assembly language appropriate in view of the processor being used. It could also be written in an interpretive environment such as Java and transported to multiple destinations to various users.

The many features and advantages of the embodiments of the present invention are apparent from the detail specification, and thus, it is intended by the appended claims to cover all such features and advantages of the invention that fall within the true spirit and scope of the invention. Further, since numerous modifications and variations were readily occurred to those skilled in the art, it is not desired to limit the invention to the exact construction and operation illustrated and described, and accordingly, all suitable modifications and equivalents may be resorted to, falling within the scope of the invention.

What is claimed is:

1. A method comprising
accessing, on a processor, a plurality of pharmacy claims associated with an individual;
generating, on a processor, a raw risk index indicative of at least one of said individual's medical costs, acute medical conditions, and variation in medical costs, by using the plurality of pharmacy claims;
processing, on the processor, the plurality of pharmacy claims to identify a plurality of compliance medications prescribed to the individual;
associating, on the processor, a regression coefficient with each compliance medication of the plurality of compliance medications;
determining, on the processor, compliance of the individual with the plurality of compliance medications to generate a plurality of compliance medication scores a compliance medication score of the plurality of compliance medication scores being associated with a compliance medication prescribed to the individual;
multiplying, on the processor, each of the plurality of compliance medication scores with an associated regression coefficient of the plurality of coefficients, the plurality of regression coefficients including the regression coefficient; and
modifying, on the processor, the raw risk index based on multiplying each of the plurality of compliance medication scores with the associated regression coefficient to generate the risk index.

2. The method of claim 1, wherein the compliance medication score is determined by summing a total supply of the compliance medication prescribed to the individual and multiplying by the regression coefficient.

3. The method of claim 2, wherein the regression coefficient is generated from a log transform.

4. The method of claim 2, wherein the regression coefficient is generated from a square-root transform.

5. The method of claim 1, wherein the compliance medication score represents compliance of the individual with the compliance medication prescribed to the individual.

6. A non-transitory computer readable medium, which when executed by one or more processors, cause the one or more processors to perform the following operations:
access a plurality of pharmacy claims associated with an individual;
generate a raw risk index indicative of at least one of said individual's medical costs, acute medical conditions, and variation in medical costs, by using the plurality of pharmacy claims;
process the plurality of pharmacy claims to identify a plurality of compliance medications prescribed to the individual;
associate a regression coefficient with each compliance medication of the plurality of compliance medications;

determine compliance of the individual with the plurality of compliance medications to generate a plurality of compliance medication scores, a compliance medication score of the plurality of compliance medication scores being associated with a compliance medication prescribed to the individual;

multiply each of the plurality of compliance medication scores with an associated regression coefficient of the plurality of coefficients, the plurality of regression coefficients including the regression coefficient; and modify the raw risk index based on multiplying each of the plurality of compliance medication scores with the associated regression coefficient to generate the risk index.

7. The non-transitory computer readable medium of claim 6, wherein the compliance medication score is determined by summing a total supply of the compliance medication prescribed to the individual and multiplying by the regression coefficient.

8. The non-transitory computer readable medium of claim 7, wherein the regression coefficient is generated from a log transform.

9. The non-transitory computer readable medium of claim 7, wherein the regression coefficient is generated from a square-root transform.

10. The non-transitory computer readable medium of claim 6, wherein the compliance medication score represents compliance of the individual with the compliance medication prescribed to the individual.

11. A system comprising:

a computing device including a processor and a memory coupled to the processor to:

access a plurality of pharmacy claims associated with an individual, generate a raw risk index indicative of at least one of said individual's medical costs, acute medical conditions, and variation in medical costs, by using the plurality of pharmacy claims, process the plurality of pharmacy claims to identify a plurality of compliance medications prescribed to the individual, associate a regression coefficient with each compliance medication of the plurality of compliance medications, determine compliance of the individual with the plurality of compliance medications to generate a plurality of compliance medication scores, a compliance medication score of the plurality of compliance medication scores being associated with a compliance medication prescribed to the individual, multiply each of the plurality of compliance medication scores with an associated regression coefficient of the plurality of coefficients, the plurality of regression coefficients including the regression coefficient, and modify the raw risk index based on multiplying each of the plurality of compliance medication scores with the associated regression coefficient to generate the risk index.

* * * * *